United States Patent [19]

Walters et al.

[11] 4,192,316

[45] Mar. 11, 1980

[54] PROGRAMMABLE ATRIO-VENTRICULAR PACER

[75] Inventors: Robert A. Walters, Murrysville; William L. Johnson, Kittanning; Gary W. Bivins, Pittsburgh, all of Pa.

[73] Assignee: ARCO Medical Products Company, Leechburg, Pa.

[21] Appl. No.: 908,296

[22] Filed: May 22, 1978

[51] Int. Cl.² ............................................. A61N 1/36
[52] U.S. Cl. ............................................. 128/419 PG
[58] Field of Search .............. 128/419 PG, 421, 422, 128/423

[56] References Cited

U.S. PATENT DOCUMENTS

| | | | |
|---|---|---|---|
| 3,783,878 | 1/1974 | Thaler et al. | 128/419 PG |
| 3,833,005 | 9/1974 | Wingrove | 128/419 PG |
| 4,049,004 | 3/1976 | Walters | 128/419 PG |
| 4,060,090 | 11/1977 | Lin et al. | 128/419 PG |

Primary Examiner—William E. Kamm
Attorney, Agent, or Firm—John C. Martin, Jr.

[57] ABSTRACT

A programmable digital atrio-ventricular pacer is provided whereby a single programming circuit is utilized for providing program control signals for control of separate ventricular and atrial pacing circuits. The atrial stimulus circuitry is controlled by a multiple bit control signal to cause derivation of atrial timing signals from the same clock signal as used for deriving ventricular stimulus pulses. A programmable digital multiplier is employed in combination with a counter to set the atrial escape interval independent of the timing of the ventricular stimulus pulses.

3 Claims, 2 Drawing Figures

PROGRAMMABLE ATRIO-VENTRICULAR PACER

BACKGROUND OF THE INVENTION

This invention lies in the field of cardiac pacers and more particularly, programmable atrio-ventricular pacers.

In the field of cardiac pacers, by far the dominant form of pacer is the demand ventricular pacer which provides stimulus pulses to a patient's ventricle in the absence of naturally occurring ventricular (QRS) heartbeats. A less frequently used type of pacer, although by now well known in the art, is the atrio-ventricular or sequential type of pacer which provides a first stimulus to the atrium to contract it and then a second stimulus to the ventricle, the second stimulus being delayed with respect to the atrial stimulus in accordance with the known A-V delay of a normal heart. In particular, this invention relates to a pacer having independent ventricular and atrial stimulating circuits which are both synchronized with respect to the activity of the patient's ventricle, i.e., the timing of the ventricular and atrial stimulus pulses is synchronized with the contraction of the ventricle, whether such contraction be naturally occurring or caused by the delivery of the ventricular stimulus pulse from the pacer itself.

Another feature that is currently gaining wider acceptance in the pacer area is that of programmed control of preselected pacer operating parameters. As is shown in the prior art, including U.S. Pat. No. 4,049,004, assigned to the same assignee, it is known that selected operating parameters may be controlled through program signals generated externally of the patient, transmitted to and received by the pacer implanted within the patient, and then transformed into appropriate control signals for control of the selected parameters. However, there remains a need for efficient utilization of such programmed control concepts in the embodiment of a programmable atrio-ventricular pacer, so that the advantages of programmable control may be extended to this more specialized form of pacer.

SUMMARY OF THE INVENTION

It is an object of this invention to provide a programmable atrio-ventricular pacer having common programming means for programming the timing of both the ventricular and atrial circuit components of the pacer.

It is another object of this invention to provide a programmable atrio-ventricular pacer utilizing digital circuitry and common programming means for controlling the generation of synchronized ventricular and atrial stimulating pulses.

It is another object of this invention to provide a programmable atrio-ventricular pacer wherein programmable digital control signals are utilized for controlling digital circuitry which in turn generates atrial stimulating pulses synchronized with the timing of the patient's ventricular contractions.

In accordance with the above objectives, there is provided a programmable digital atrio-ventricular pacer wherein a signel programming circuit provides digital control signals for control of separate ventricular and atrial pacing circuits. The atrial stimulus generating circuit utilizes digital circuitry for obtaining a timing signal controlled by a portion of the digital control signal, the timing signal in turn being used to generate atrial stimulus pulses synchronized with the occurrence of ventricular contractions.

DESCRIPTION OF THE PREFERRED EMBODIMENT

Figure 1:
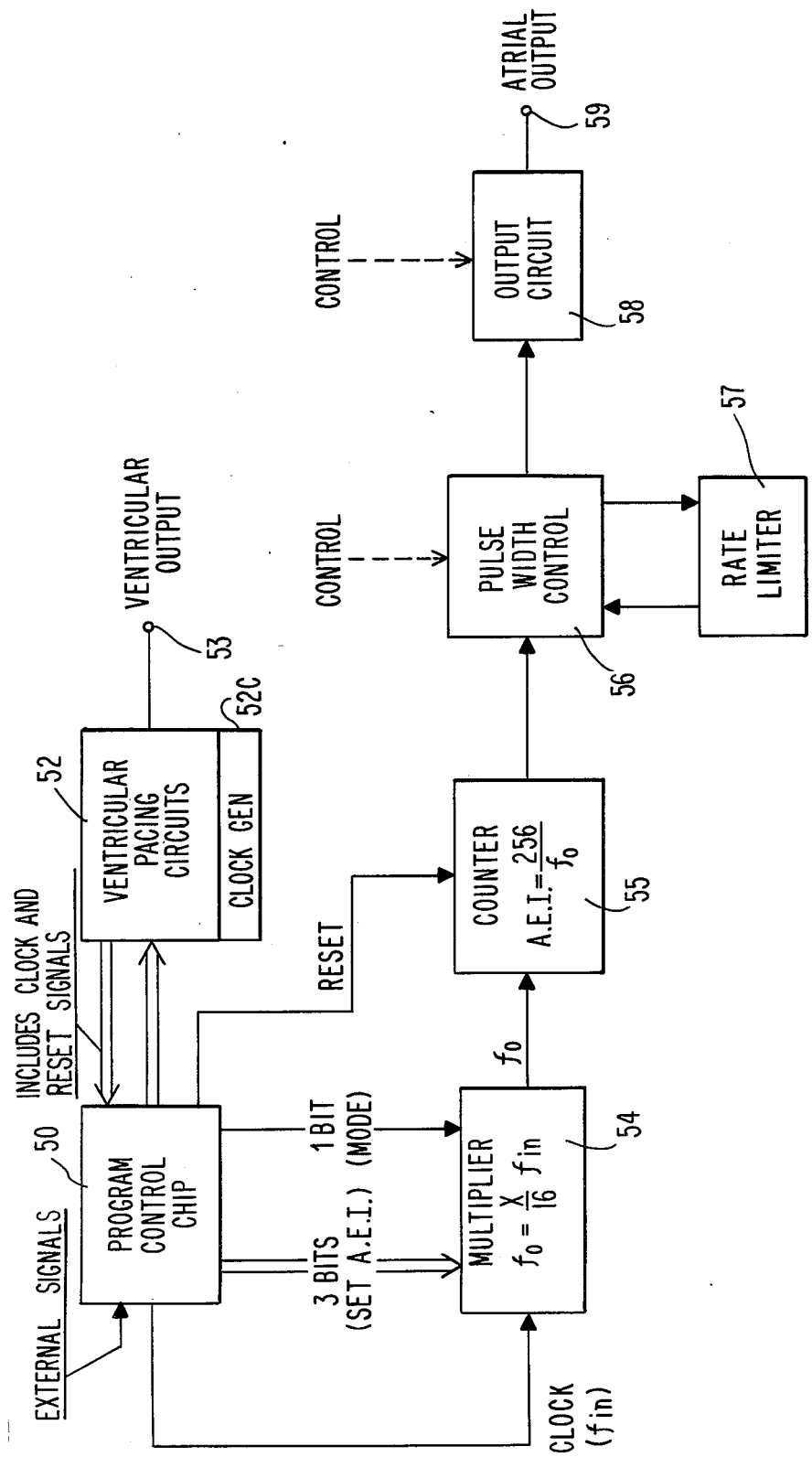
FIG. 1 is a block diagram of the primary elements of the pacer.

Referring now to FIG. 1, there is shown a block diagram of the primary elements of the pacer of this invention. The key control element is a program control chip 50, which is suitably a custom IC chip such as employed to carry out the program control functions disclosed in U.S. Pat. No. 4,049,004, assigned to the same assignee. The circuitry of this chip provides for receiving externally generated parameter control signals, suitably in the form of a multiple bit data word. The data encoded on the externally received signal is transferred into a register, wherein the logic states of the respective stages of the register are utilized singly or in combination to derive control signals for control of various different operating parameters. In the normal ventricular demand pacer, control signals are transmitted to the ventricular pacing circuits 52 to control selected operating parameters of those circuits, which in turn provide the ventricular output at node 53 in the form of on demand stimulus signals. The circuitry embraced within block 52 includes a clock pulse generator, which is used for controlling the basic timing arrangement of the ventricular pacing circuits. The clock pulse output is also transmitted through the chip 50, and as seen in utilized in the atrial circuitry. The combination of control chip 50 and ventricular demand pacing circuitry 52, and the circuit details thereof, are fully disclosed in the aforementioned U.S. Pat. No. 4,049,004.

In the preferred embodiment, three bits of the programmable binary control word stored within program control chip 50 are utilized for determining the atrial escape interval. Three bits of information provides capacity for eight different control states, or eight different atrial escape intervals, if such are desired. If fewer or more different escape intervals are desired, fewer or more bits from the program control chip can be utilized for this function. Another bit from the stored control signal in chip 50 is utilized to establish the operating mode of the atrial portion of the pacer, i.e., whether the atrial circuit is enabled or disabled. The control data bits, along with clock pulses at a predetermined rate are provided from chip 50 and inputted to a digital multiplier 54, which provides an output $f_o$ which is a programmed multiple of the clock pulse repetition frequency ($f_{in}$). The multiple, designated as X/16, is determined by the information transmitted in the three bits allocated for setting the atrial escape interval. The output signal, which is a pulse train at a rate of $f_o$, is inputted to a digital counter 55, which is wired to count to 256, thereby acting as a frequency divider. The atrial escape interval (A.E.I.), or the time required to produce an atrial output pulse, is the time period of one cycle of the $f_o$ signal multiplied by 256, as indicated in block 55. The output from block 55 is connected to a pulse width control circuit 56, which establishes and sets the time duration of the output pulse. Connected to pulse width control circuit 56 is a rate limiter circuit 57, for disabling transmission through pulse width control circuit 56 when the atrial pulse rate exceeds a predetermined limit. The output of pulse width control circuit 56 is connected to output circuit 58, which provides the atrial output at terminal 59. Circuits 56, 57 and 58 may be conventional fixed parameter circuits, or they may also be programmably controlled from chip 50, as indicated by the dashed lines designated "CONTROL".

Figure 2:
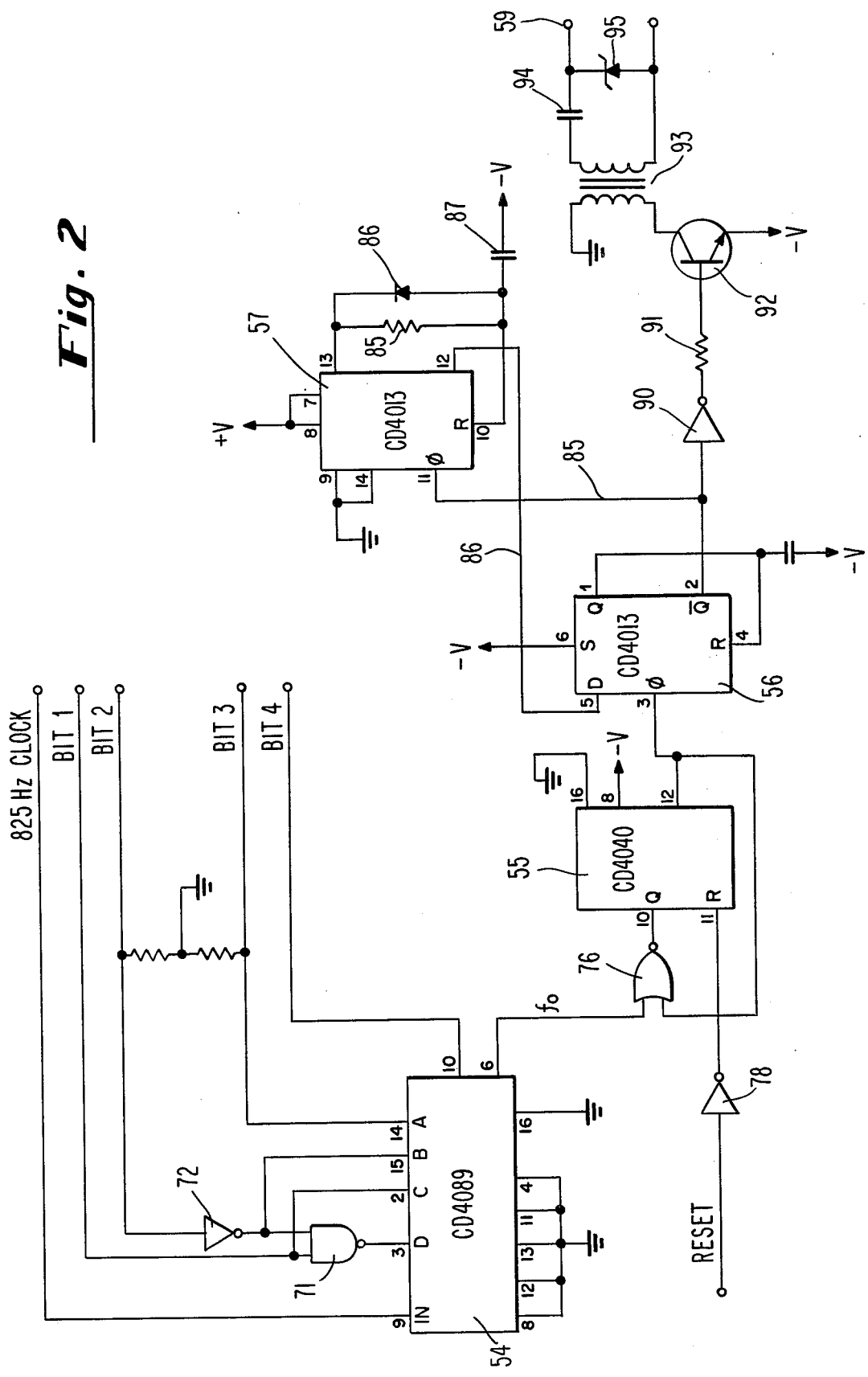
FIG. 2 is a detailed schematic diagram of the atrial circuit portion of the pacer.

Referring now to FIG. 2, there is shown a detailed schematic diagram of the atrial circuit portion of the pacer of this invention. The three bit control signal is shown as consisting of bits 1, 2 and 3 connected to three different terminals which are in connection with respective stages of a register in chip 50 where the binary control word is stored. These terminals are connected through a logic arrangement comprising NAND gate 71 and inverter 72. The output of this logic arrangement is connected to inputs A, B, C and D respectively of multiplier 54. Multiplier 54 is suitably a commercially available IC, type CD4089, with its pins connected as shown. The multiplier also receives an 825 Hz clock signal and a fourth bit which controls the mode of operation. Bit 4 either enables or disenables multiplier 54 from providing an output, depending upon its logic state.

The truth table, or logic arrangement of the combination of NAND gate 71, inverter 72 and IC 54, is as follows:

| Bit 1 | Bit 2 | Bit 3 | D | C | B | A | X |
|---|---|---|---|---|---|---|---|
| 0 | 0 | 0 | 1 | 0 | 1 | 0 | 10 |
| 0 | 0 | 1 | 1 | 0 | 1 | 1 | 11 |
| 0 | 1 | 0 | 1 | 0 | 0 | 0 | 8 |
| 1 | 0 | 0 | 0 | 1 | 1 | 0 | 6 |
| 1 | 0 | 1 | 0 | 1 | 1 | 1 | 7 |
| 1 | 1 | 0 | 1 | 1 | 0 | 0 | 12 |

In other words, the binary multiplier, X, will be either 6, 7, 8, 10, 11, or 12, depending upon the configuration of the 3 bit data signal. As indicated previously, circuit 54 has an overall multiplier factor of X/16, such that the repetition rate $f_0$ of the pulse output is $(X/16)f_{in}$.

The output from multiplier 54 is connected through NOR gate 76 to the input of counter 55. NOR gate 76 is enabled when a reset signal has been transmitted through inverter 78 to the reset terminal. The reset signal is the same reset signal used in the ventricular circuit, i.e., it is generated following normal timeout of the ventricular timing circuitry, or detection of a naturally occurring QRS signal. Counter 55 is suitably a commercially available IC, type CD4040, connected as shown in the drawing, and counts to 256. Thus, for clock pulses provided at 825 Hz, the Atrial Escape Interval (in ms) is as follows:

| X | AEI (ms) |
|---|---|
| 6 | 830 |
| 7 | 710 |
| 8 | 620 |
| 10 | 500 |
| 11 | 450 |
| 12 | 415 |

The output of counter 55 is connected to a first D type flip-flop 56, suitably one-half of an IC, type CD4013. Flip-flop 56 is connected as a "one shot", and its output at terminal $\overline{Q}$ is connected along line 85 to a second D type flip-flop 57, which is suitably the other flip-flop of the type CD4013 IC. Flip-flop 57 is combined with resistor 85 and diode 86 connected between its terminals 10 and 13, with capacitor 87 connected between terminal 10 and −V supply. This arrangement provides a rate limit one shot circuit. The output of terminal 12 of flip-flop 57, connected along line 86 to the D input of flip-flop 56, effectively disables flip-flop 56 whenever the rate exceeds the predetermined limit.

The output of flip-flop 56 is also connected through inverter 90 and resistor 91 to the base of transistor 92. The collector of transistor 92 is connected to a first winding of transformer 93, the output winding being connected through capacitor 94 to output terminal 59. Diode 95 is connected for peak limiting purposes, as is conventional.

In practice, the gate elements 71, 72, 76, 78, and 90 are suitably provided by a single IC, type Mc14572.

There is thus shown apparatus which meets the objects stated above, namely a pacer which uses a common timing source for independently controlling both an atrial stimulus circuit path and a ventricular stimulus circuit path. Both paths are programmable from a single program control circuit, providing for maximum flexibility in programming the variables of the bifocal pacer. The atrial escape interval is obtained by employing binary program control data to control the repetition rate of the basic timing signal from which the atrial output pulses are obtained.

We claim:

1. Programmable digital pacer apparatus for providing and delivering synchronized atrial and ventricular stimulus pulses to a patient's heart, said apparatus comprising a ventricular pacing circuit comprising demand generator means for producing ventricular stimulus pulses in the absence of natural heartbeats, and an atrial pacing circuit for generating and delivering atrial stimulus pulses in the absence of natural heartbeats, said ventricular pacing circuit and atrial pacing circuit being synchronized in their timing, said pacer being characterized by having digital programming means for receiving external parameter control signals and generating a plural bit binary word therefrom, ventricular control means for deriving ventricular control signals from a predetermined number of the bits of said word and controlling predetermined parameters of said ventricular pacing means therewith, and atrial control means for deriving atrial control signals from a second predetermined portion of said binary word and controlling predetermined operating parameters of said atrial pacing means therewith, said pacer further comprising a clock generator connected to deliver clock signals to said ventricular pacing circuit and to said atrial pacing circuit, said ventricular pacing circuit having means for determining the rate of said ventricular stimulus pulses as a function of both said clock signals and said ventricular control signals and said atrial pacing circuit having means for determining the rate of said atrial stimulus pulses as a function of both said clock pulses and said atrial control signals, said atrial pacing circuit further comprising atrial escape interval means adapted to provide a timing signal for timing the generation of said atrial stimulus pulses, and means for resetting said atrial escape interval means in synchronization with the operation of said ventricular pacing circuit, said atrial escape interval means being characterized by having circuitry which disables its operation following delivery of an atrial stimulus pulse until it is reset by a synchronizing signal from said ventircular pacing circuit.

2. The pacer apparatus as described in claim 1, wherein a 3 bit binary signal is connected from said programming means to said atrial pacing circuit for controlling the escape interval of said atrial stimulus pulses.

3. The programmable pacer as described in claim 1, wherein said programming means comprises means for connecting a binary signal to said atrial pacing circuit for controlling whether said atrial pacing circuit is in a state of operation or in a disabled state.

* * * * *